United States Patent [19]

Lindauer

[11] Patent Number: 5,776,561
[45] Date of Patent: Jul. 7, 1998

[54] FRAGRANCE-DISPENSING SILK FLOWER COMBINATION

[75] Inventor: Jerome I. Lindauer, Hillsdale, N.J.

[73] Assignee: Bath & Body Works, Inc., Reynoldsburg, Ohio

[21] Appl. No.: 828,565

[22] Filed: Mar. 31, 1997

[51] Int. Cl.$^6$ .................................................. A41G 1/00
[52] U.S. Cl. ...................... 428/24; 428/34.1; 428/905; 239/34
[58] Field of Search ................ 428/24, 26, 34.1, 428/905; 239/34

*Primary Examiner*—Alexander Thomas
*Attorney, Agent, or Firm*—Colucci & Umans

[57] ABSTRACT

A fragrance-dispensing artificial flower combination has a cylindrical container with an open upper end and a closed lower end. A volatile liquid fragrance is in the container and a piston is slidably mounted in the container for closing the container over the fragrance. The piston has an opening therethrough, between the open upper end of the container and the fragrance in the container. A tube having a lower open end extending into the open end of the piston, has an upper open end. An absorbent material button receives the upper end of the tube, the button having a lower surface pierced by a passage into which the upper end of the tube extends, means defining an artificial flower connected around the button and a sleeve around the tube extending from the container to the flower for simulating a stem of the flower, the tube being operable to push the piston downwardly into the container for forcing liquid fragrance from the container through the piston and into the porous plastic button for saturating the button to dispense the fragrance from the button.

20 Claims, 2 Drawing Sheets

5,776,561

1

FRAGRANCE-DISPENSING SILK FLOWER COMBINATION

FIELD AND BACKGROUND OF THE INVENTION

U.S. Pat. No. 355,982 (1887) discloses a hollow stem that extends from the heart of an artificial flower into a reservoir of liquid perfume. The heart of the flower is made from an absorbent material such as cotton. The hollow tube may enclose an absorbent wick for carrying the liquid from the reservoir to the heart of the flower, or the tube may communicate with a squeeze bulb that causes the liquid to be sprayed over the absorbent when the bulb is squeezed.

U.S. Pat. No. 5,077,102 discloses a scented artificial flower with a stem that extends from the ovary of the flower into a reservoir of perfume. A wick within the stem connects the perfume reservoir to the ovary and stamen elements of the flower, which are both constructed of a wicking material. The perfume may be supplied to the ovary and stamens by capillary action or pressure supplied by a pump. Alternatively, the stem may be a hollow tube that supplies the perfume to the ovary and stamens by gravity, from an elevated container.

U.S. Pat. No. 4,919,981 discloses an air freshener in the form of a decorative vase containing one or more artificial flowers. A stem-like wick extends between a reservoir of liquid air freshener within the vase, and a vapor dispenser. The vapor dispenser may take the form of flat leaf-like pad elements or sponge-like elements formed and colored to resemble an artificial flower or a portion thereof. The reservoir may be partitioned into a number of sections each capable of containing a liquid having a different scent.

U.S. Pat. No. 4,928,881 discloses a conventional air freshener, shaped to resemble a flower. The air freshener includes a wick in communication with a liquid reservoir. The wick is formed by a bundle of strands of polyester or other suitable material capable of carrying the liquid by capillary action from the reservoir to a diffusing site. The wick directly disperses the air freshener to the air at the diffusing site without the intervention of a separate scent pad.

U.S. Pat. No. 5,242,111 discloses a wick type liquid dispensing device suitable for use in dispensing an air freshening liquid. The wick is formed from an absorbent material located within a hollow impermeable tube, the liquid supply is separated from the wick prior to use by a containment element, which is breached to allow the liquid to contact the wick and travel to an imminator that evaporates the liquid into the air. The containment element may take the form of a removable clip or a breakable internal seal or membrane.

U.S. Pat. Nos. 4,419,326 and 4,413,779 disclose a vapor dispersing device and process which regulates the evaporative dispersion of a fragrance. Over time, the nonvolatile components of a fragrance solution tend to build-up on the porous element from which a fragrance is dispersed. This clogs the pores of the porous element, limiting the dispersion of the fragrance. These patents attempt to solve this problem by providing a porous material that has been treated with an occluding agent that evaporates from the porous element at approximately the same rate as the build-up of the nonvolatile fragrance components. The porous element is made of porous polyethylene and is sealed to a pressurized container to increase flow to the porous element.

U.S. Pat. No. 3,400,890 discloses an artificial flower or potted plant having a component formed from an absorbent

2 hydrogel capable of absorbing and storing the solids in a fragrant essence solution. The hydrogel releases the fragrance to the air when it is exposed to an appropriate solvent. The hydrogel may be present in a portion of the flower, with the solvent supplied to this part of the flower through a wick in communication with a solvent reservoir. Alternatively, the hydrogel may be provided within the base of an artificial potted plant where it may be exposed to the solvent, in which case the fragrance will not emanate directly from the flower portions of the plant.

U.S. Pat. No. 5,081,104 discloses an air fragrance dispenser including a reservoir of a volatile fragrance solution, a diffuser surface from which the fragrance is dispersed into the air, a wick for transporting the fragrance from the reservoir to the diffuser by capillary action, and a particular chemical composition for regulating the fragrance evaporation rate.

When it was attempted to use capillary action to draw the fragrance from a lower reservoir to an artificial flower, it was found impossible to convey sufficient amounts of fragrance to act as an air freshener when the stem of the flower was longer than approximately 10 inches, and impossible when the stem was 18 inches long.

A need remains for a simple and economical arrangement that dispenses fragrance and that has the appearance of a decorative silk flower, and which avoids the complexity and expense of the prior art.

SUMMARY OF THE INVENTION

An object of the present invention is to provide a fragrance-dispensing artificial flower combination or arrangement, comprising a pump cylinder container having an upper end closed by a piston, a volatile liquid fragrance in the container, a tube having a lower open end engaged with the piston which can be pressed against the liquid in the container, the tube having an upper open end, an absorbent member or artificial pistil for receiving the upper end of the tube, the pistil being made of solid absorbent material such as porous synthetic or natural material, and means around the tube and pistil and supported by the tube for simulating a flower with stem.

A further object of the present invention is to provide a fragrance-dispensing artificial flower arrangement, in particular, a silk flower, which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which an embodiment of the invention is illustrated.

DESCRIPTION OF THE PREFERRED EMBODIMENT

Figure 1:
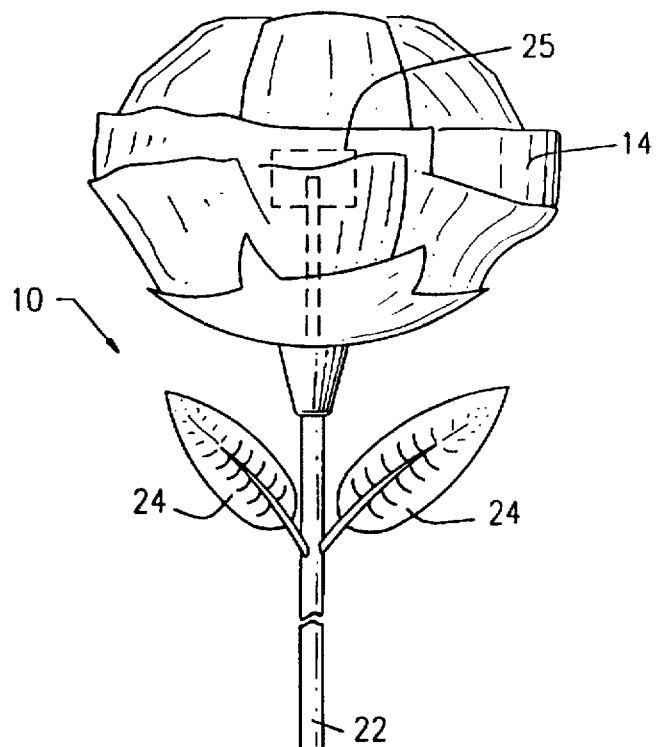
FIG. 1 is a schematic, partly sectional view of an artificial flower combination and arrangement for dispensing fragrance, according to the present invention.
Figure 1:
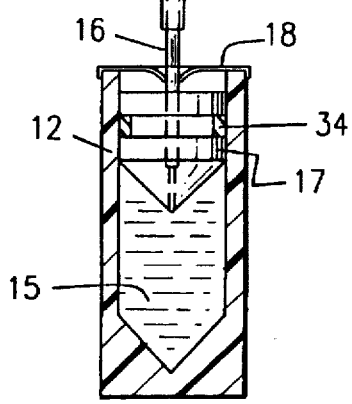
Figure 3:
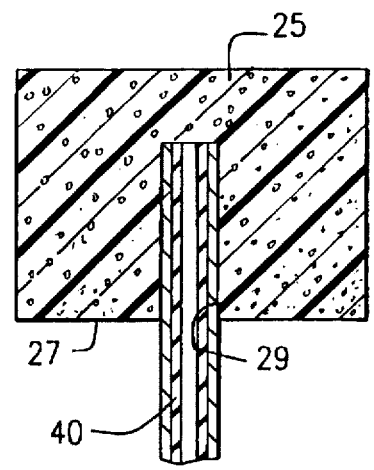
FIG. 3 is an enlarged sectional view of the upper end of the tube inserted into a porous member in the flower.
Figure 2:
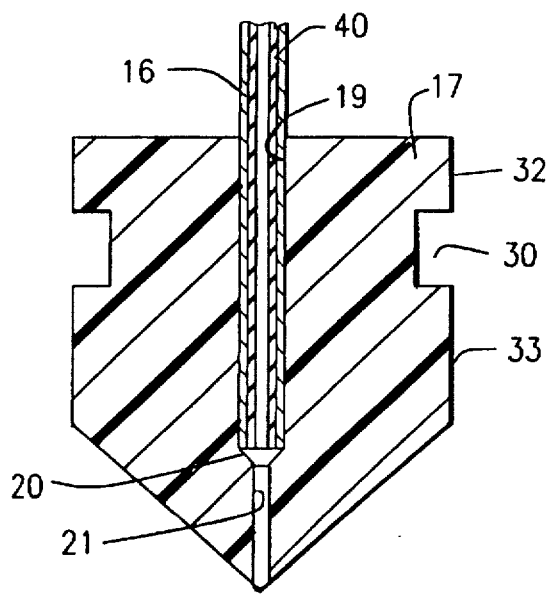
FIG. 2 is an enlarged sectional view of the lower end of a tube inserted into a piston of the invention.

Referring to the drawings in particular, the invention embodied in FIGS. 1–3 comprise a fragrance-dispensing artificial flower combination generally designated 10 having a lower end with a pump mechanism having a container 12 made of plastic, for example, and an upper end with a flower structure 14.

The container 12, in the form of a rigid pump cylinder, is at least partially filled with a volatile liquid fragrance 15. It is made of ABS plastic, nylon or other rigid water tight material.

A tube 16 made of flexible but self supporting material such as brass or rigid but bendable plastic, has a lower end extending into a piston 17 mounted for sliding movement in the container 12 and placed above the liquid 15. Container 12 has an outer cylindrical surface which is advantageously covered with foil , paint or other decorative cover and can be placed in a vase, such as a bud vase or the like. The upper end of container 12 is covered at 18 by a hermetically sealed foil cover, to avoid direct evaporation of the liquid 15 into the air before the pump is used. Foil 18 is thin enough so that it can be ruptured by being pierced by the lower end of tube 16 which is moved downwardly into a cylindrical opening or bore 19 in the piston 17 which is upwardly open for receiving tube 16. Bore 19 extends only partly through the central axis of piston 17. Just below the center of the piston, bore 19 tapers inwardly at 20 and communicates with a small diameter bore 21 which extends the rest of the way through piston 17 in order to communicate the interior of the tube 16 with the reservoir of liquid 15 positioned below piston 17.

Tube 16 is covered by a sheath or sleeve 22 which has an outward appearance that mimics the stem of a flower, and, for example, has a green coloring. Sleeve 22 is advantageously made of flexible plastic.

One or more artificial and non-functional plastic branches and leaves 24 are attached to the outer surface of sheath 22, again to mimic the branches and leaves of a flower.

A cylindrical porous plastic button 25 receives the upper end of the tube 16. Button 25 may be shaped to mimic the pistil of a flower or may simply be cylindrical and has a substantially flat lower surface 27 which is pierced by an opening that leads into the pistil 25 (see FIG. 3). Pistil 25 is advantageously made of absorbent material such as microporous polyethylene, cellulose or felt so that it can absorb and then dispense the volatile liquid fragrance 15 which is pumped along tube 16 from container 12 in the manner to be described. The porous polyethylene, cellulose or other absorbent material absorbs the volatile liquid and then disperses the liquid by evaporation from the outer surface of button 25.

To further enhance the movement of liquid fragrance from cylinder 12, outer metal or plastic tube 16 contains an inner, soft synthetic (e.g. polyurethane) tube 40, that lines the full length of tube 16.

The inside diameter of tube 16 is not critical. It may be about 1/16 inches in the example shown, or about 1/32 to 1/8 inches in diameter. Inner tube 40 has an inside diameter of 1/64 to 1/16 inch to freely pass liquid fragrance.

Depending on the type of flower 14, some petals may envelope the button or pistil 25, for example, the inner petals of a simulated rose. Any other arrangements of stems, petals and other artificial flower parts can also be used in conjunction with the invention. Flower 14 may be silk or plastic or a combination thereof.

It has been found that an active pump of the present invention is essential to transport volatile liquid fragrance 15 from container 12 all the way along tube 16, particularly where the tube and its' covering stem sheath 22 has a length of over 10 inches or a length in the range of 10–25 inches. At these lengths, simply capillary action was found insufficient to transport enough volatile liquid to the porous button 25 to produce an air freshening effect.

In operation, a new pump unit containing liquid 15 with its' container 12 and piston 17 covered by un-pierced foil 18, is supplied to a user. The user also has an artificial flower 14 with its' tube 16 extending downwardly from the lower end of decorative sheath 22. As noted above, the lower end of tube 16 is used to pierce foil 18 and is inserted into bore 19. Tube 16 is pushed further downwardly, thereby pressing piston 17 so that it slides downwardly in container 12. This produces increased pressure in the container which forces fragrance 15 up through bore 21 and into the hollow tube 40. The air in the tube is displaced as it moves thought the porous body of button 25, until fragrance 15 reaches the button and saturates the porous material of the button. This dispenses fragrance by evaporation from the outer surface of button 25.

Piston 17 is pushed all the way to the bottom of container 12 and totally displaces all of the fragrance 15. The volume of fragrance used is about 1.5 to about 1.8 ml and about matches the volume of the inside (lumen) of tube 40 plus the volume of pores in button 12 so that the button becomes fully charged with liquid fragrance. When the user feels that insufficient air freshening effect is being achieved, the old pump mechanism is removed and a new one is used. The lower end of piston 17 is conical and corresponds to the shape of the interior of chamber 12 at the lower end of the chamber. In this way, all of the liquid 15 can be dispensed by pressing piston all the way down into the bottom of container 12 for fully charging the flower before use with each new pump mechanism.

To help facilitate sealing of the outer surface of piston 17 to the inner surface of container 12, piston 17 is provided with a groove 30 between upper and lower annular sections 32, 33. Piston 17 is advantageously made of hard plastic such as nylon and can be firmly sealed against the inner surface of container 12 which can be made of different or the same hard plastic, for example, ABS plastic or nylon.

If needed, an O-ring 34 may be provided in groove 30 to further improve the seal. Alternatively, the outside diameter of one or both annular sections 32 and 33 may be selected to be slightly larger than the inside diameter of cylindrical container 12, so that the resiliency of the synthetic materials themselves form the seal.

An advantageous composition for the volatile liquid fragrance 15 is:

| ingredient | % w/w | range |
|---|---|---|
| Denatonium Benzoate (Bitrex) | 0.02% | 0.01–0.03% |
| Phenylethyl alcohol | 30% | 20%–40% |
| Rose Oxide | 22% | 18%–26% |
| Beta Ionone | 15% | 10%–20% |
| Trans, trans-delta-damascone | 33% | 20%–40% |

Total liquid about 1.5 grams or 1.667 ml (for liquid with specific gravity of about 0.9%).

Bitrex is used as an aversive agent to prevent accidental ingestion of the liquid. The last four ingredients are fragrance.

Other possible additives to the volatile liquid fragrance composition are water soluble alcohols, petroleum distillates or cyclomethicones to be used as volatility enhancers.

At room temperature, the fragrance has a viscosity in the range of 0.5 to 150 CS so that it will travel along tube 16, 40 and saturate button 25 easily.

Figure 4:
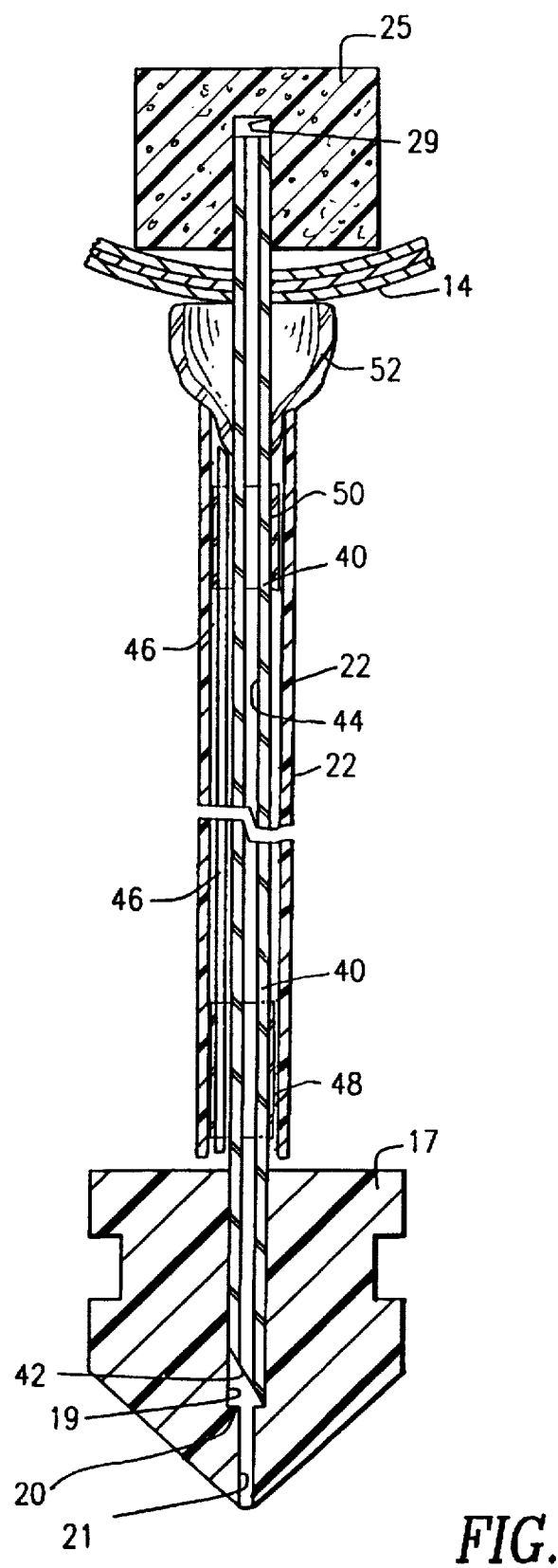
FIG. 4 is a sectional view of another embodiment of the invention.

Another embodiment of the invention illustrated in FIG. 4 replaces the stiffening means in the form of a stiff, bendable tube 16 in FIGS. 1–3, with a bendable wire 46 which extends almost the full length of the tube 40 and which is held to the tube at a plurality of locations along its length, by plastic bands 48 or bands made of tape or other mechanism for holding the wire 46 against and along the tube 40 to give it structural strength so that it can be bent into any desired shape, to mimic the bend in a flower stem. As with the embodiment of FIG. 2, the stiffened tube 40 is covered by a sheath 22 that looks like the outer surface of a flower stem. A cup 52 extends from the upper end of sheath 22 and against the bottom layers of petals in flower 14, to enhance the illusion that the product is a real flower. The stiffening means in the form of wire 46 extend only from the top of piston 17 to the bottom of cup 52 to avoid interfering with the piercing of the piston with the lower end of the tube and the piercing of the button with the upper end of the tube.

In the embodiment of FIG. 4, tube 40 is also cut at an angle at 42, to improve its ability to pierce the foil 18 (in FIG. 1) and to improve the ease with which it engages the upper end of bore 19 and is seated in step 20 to permit downward movement of piston 17.

While a specific embodiment of the invention has been shown and described in detail to illustrate the application of the principles of the invention, it will be understood that the invention may be embodied otherwise without departing from such principles.

What is claimed is:

1. A fragrance-dispensing artificial flower combination, comprising:

a cylindrical container having an open upper end and a closed lower end;

a volatile liquid fragrance in the container;

a piston slidably mounted in the container for closing the container over the fragrance, the piston having an opening therethrough, between the open upper end of the container and fragrance in the container;

a tube having a lower open end extending into the open end of the piston, the tube having an upper open end;

an absorbent material button for receiving the upper end of the tube, the button having a lower surface pierced by a passage into which the upper end of the tube extends;

means defining an artificial flower connected around the button; and a sleeve around the tube extending from the container to the flower for simulating a stem of the flower, the tube being operable to push the piston downwardly into the container for forcing liquid fragrance from the container through the piston, along the tube and into the porous button for saturating the button to dispense the fragrance from the button.

2. A combination according to claim 1 wherein the button is made of at least one of microporous polyethylene, cellulose or felt.

3. A combination according to claim 1 including a pierceable seal over the upper open end of the container for sealing the container, the seal being pierceable by the lower end of the tube.

4. A combination according to claim 1 wherein the cylindrical container is conical in the lower closed end thereof, the piston having a conical lower end movable into the conical lower end of the container for forcing most of the fragrance from the container as the piston is slid downwardly in the container.

5. A combination according to claim 1 wherein the piston includes an annular groove around its outer surface.

6. A combination according to claim 1 including a plurality of cylindrical containers, each with a slidable piston and containing a volatile liquid fragrance, in combination with the tube, for use when the fragrance in one of the containers has been exhausted.

7. A combination according to claim 1 wherein the opening through the piston has a large diameter portion of a diameter for receiving the lower end of the tube, and a small diameter portion below the large diameter portion for passing fragrance from the container through the piston and into the tube.

8. A combination according to claim 1 wherein the button is cylindrical and has flat upper and lower surfaces.

9. A combination according to claim 1 wherein the volatile liquid fragrance contains about 0%–30% by weight solvent and about 10% to 100% by weight fragrance.

10. A combination of claim 9 wherein the button is made of porous polyethylene, cellulose or felt.

11. A combination of claim 10 wherein the opening through the piston has a large diameter portion for receiving the tube and a small diameter portion for passing fragrance from the container through the piston and into the tube.

12. A combination according to claim 11 wherein the closed lower end of the container has a conical shape and the lower end of the piston has a conical shape so that when the piston is slid to the bottom of the container, most of the fragrance is discharged from the container.

13. A combination according to claim 12 wherein the piston has an annular groove around its outer surface.

14. A combination according to claim 9 including an aversive agent and a volatility enhancer.

15. A combination according to claim 14 wherein the liquid fragrance has a viscosity of about 0.5 to about 150 CS.

16. A combination according to claim 1 wherein the tube comprises an outer bendable member and an inner synthetic tube and is from about 10 to about 25 inches long.

17. A combination according to claim 16 wherein the tube comprises an outer bendable member and an inner synthetic tube and is from about 10 to about 25 inches long.

18. A combination according to claim 16 wherein the bendable member comprises a bendable wire extending along the tube and means for holding a wire to the tube.

19. A combination according to claim 1 wherein the bendable member comprises a bendable tube around the synthetic tube.

20. A combination according to claim 1 wherein the volume of the liquid fragrance in the container is about equal to the volume of the lumen of the tube plus a volume of pores in the absorbent material so that when the piston is slid to the bottom of the container, the absorbent material and the tube are completely filled with fragrance.

* * * * *

UNITED STATES PATENT AND TRADEMARK OFFICE
Certificate

Patent No. 5,776,561                                                                     Patented: July 7, 1998

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Jerome I. Lindauer, Hillsdale, NJ; Ashok V. Joshi, Salt Lake City, UT; John H. Gordon, Salt Lake City, UT; Giorgio Di Palma, Draper, UT; John J. McEvoy, Sandy, UT; and Truman Wold, Salt Lake City, UT.

Signed and Sealed this Ninth Day of November, 1999.

ELLIS P. ROBINSON
                                                                                           *Supervisory Patent Examiner*
                                                                                                     Art Unit 1772